(12) United States Patent
Snutch

(10) Patent No.: US 6,492,375 B2
(45) Date of Patent: *Dec. 10, 2002

(54) PARTIALLY SATURATED CALCIUM CHANNEL BLOCKERS

(75) Inventor: Terrance P. Snutch, Vancouver (CA)

(73) Assignee: NeuroMed Technologies, Inc., Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/818,063

(22) Filed: Mar. 26, 2001

(65) Prior Publication Data

US 2001/0029258 A1 Oct. 11, 2001

Related U.S. Application Data

(63) Continuation of application No. 09/476,929, filed on Dec. 30, 1999, now abandoned, which is a continuation-in-part of application No. 09/401,699, filed on Sep. 23, 1999, now Pat. No. 6,294,533, which is a continuation-in-part of application No. 09/107,037, filed on Jun. 30, 1998, now Pat. No. 6,011,035.
(60) Provisional application No. 60/172,765, filed on Dec. 20, 1999.

(51) Int. Cl.$^7$ ..................... A61K 31/495; A61K 31/445
(52) U.S. Cl. ....................................... 514/255; 514/315
(58) Field of Search ................................. 514/255, 315

(56) References Cited

U.S. PATENT DOCUMENTS

| | | | | |
|---|---|---|---|---|
| 3,288,795 A | 11/1966 | Irikura et al. | ................ | 260/268 |
| 4,188,485 A | 2/1980 | Kukla | ......................... | 546/202 |
| 4,918,073 A | 4/1990 | Ruger et al. | ................ | 514/255 |
| 5,292,726 A | 3/1994 | Ashton et al. | ................ | 514/85 |
| 5,386,025 A | 1/1995 | Jay et al. | ..................... | 536/23.5 |
| 5,428,038 A | 6/1995 | Chatterjee et al. | ........... | 514/253 |
| 5,623,051 A | 4/1997 | Catterall et al. | ........... | 530/324 |
| 5,646,149 A | 7/1997 | Hellberg et al. | ............ | 514/253 |
| 5,703,071 A | 12/1997 | Itoh et al. | .................... | 514/218 |
| 6,011,035 A | 1/2000 | Snutch et al. | ............. | 514/231.5 |
| 6,294,533 B1 * | 9/2001 | Snutch et al. | ............. | 514/231.2 |

FOREIGN PATENT DOCUMENTS

| | | |
|---|---|---|
| EP | 0 187 524 | 7/1986 |
| EP | 0 458 387 | 11/1991 |
| ES | 504 202 | 1/1983 |
| ES | 514 167 | 4/1983 |
| GB | 1 513 883 | 6/1978 |
| WO | WO 99 15129 | 4/1999 |
| WO | WO 99 25686 | 5/1999 |
| WO | WO 99/43658 | 9/1999 |

OTHER PUBLICATIONS

Bourinet et al., "Splicing of $\alpha_{1A}$ Subunit Gene Generates Phenotypic Variants of P– and Q–Type Calcium Channels," Nature Neuroscience (1999) 2:407–415.

Breitenbucher et al., Tetrahedron Letters (1998) 39:1295–1298.

Cohan et al., "Depolarization–Induced Presynaptic Calcium Accumulation May Occur by an N–Type Channel that is Blocked by Flunarizine," Annals of the New York Academy of Sciences (1991) 635:397–399.

(List continued on next page.)

Primary Examiner—Raymond Henley, III
(74) Attorney, Agent, or Firm—Morrison & Foerster LLP

(57) ABSTRACT

Compounds of the formula

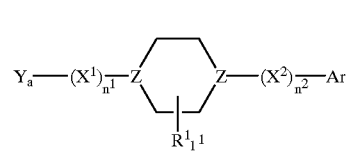

(1a)

or

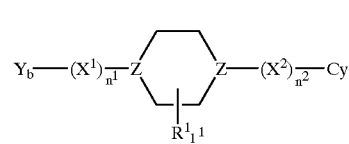

(1b)

or the salts thereof,
wherein each Z is independently N or CH, but one Z must be N;
wherein $n^1$ is 1 and $n^2$ is 0 or 1;
$X^1$ and $X^2$ are linkers;
Ar represents one or two substituted or unsubstituted aromatic or heteroaromatic rings, and
Cy represents one or two substituted or unsubstituted aliphatic cyclic or heterocyclic rings, or consists of one substituted or unsubstituted aliphatic cyclic or heterocyclic ring and one substituted or unsubstituted aromatic or heteroaromatic ring;
each of $Y_a$ and $Y_b$ is two substituted or unsubstituted aromatic or heteroaromatic rings, or can be two substituted or unsubstituted aliphatic cyclic or heterocyclic rings or consists of one substituted or unsubstituted aliphatic cyclic or heterocyclic ring and one substituted or unsubstituted aromatic or heteroaromatic ring;
with the proviso that said rings cannot both be phenyl when both Ar includes a single phenyl ring and $X^1$ contains less than 5C;
and with the proviso that formula (1b) must contain at least one aromatic or heteroaromatic ring;
$1^1$ is 0 or 1;
$R^1$ is substituted or unsubstituted alkyl (1–6C), substituted or unsubstituted aryl (6–10C) or substituted or unsubstituted arylalkyl (7–16C) optionally containing 1–4 heteroatoms selected from the group consisting of halo, N, P, O, and S or may independently be halo, OR, SR, $NR_2$, OOCR, NROCR, COR, COOR, $CONR_2$, $CF_3$, CN or $NO_2$, wherein R is H or alkyl (1–6C).

46 Claims, No Drawings

OTHER PUBLICATIONS

Cribbs et al., "Cloning and Characterization of α1H from Human Heart, A Member of the T–Type $Ca^{2+}$ Channel Gene Family," Circulation Research (1998) 83:103–109.

Database WPI Week 9711, Derwent Publications Ltd., London, GB; Abstract JP09 003067, XP002133055 (Hisamitsu Pharm Co Ltd.) Jan. 7, 1997.

De Waard et al., "Structural and Functional Diversity of Voltage–Activated Calcium Channels," Ion Channels (Narahashi, T. ed. Plenum Press, NY 1997) 4:41–87.

Dhainaut et al., "New Triazine Derivatives as Potent Modulators of Multidrug Resistance," J Med Che (1992) 35:2481–2496.

Dooley, "Lomerizine Kanebo KK" Current Opinion in CPNS Investigational Drugs (1999) 1(1):116–125.

Dunlap et al., "Exocytotic $Ca^{2+}$ Channels in Mammalian Central Neurons," Trends Neurosci (1995) 18:89–98.

Estep et al., "Synthesis and Structure–Activity Relationships of 6–Heterocyclic–Substituted Purines as Inactivation Modifiers of Cardiac Sodium Channels," J Med Chem (1995) 38:2582–2595.

Galizzi et al., "Neuroleptics of the Diphenylbutylpiperidine Series are Potent Calcium Channel Inhibitors," Proc Natl Acad Sci USA (1986) 83: 7513–7517.

Glamkowski et al., "Synthesis of 3–(4–Acylaminopiperazin–1–ylalkyl) Indoles as Potential Antihypertensive Agents," J Med Chem (1977) 20(11):1485–1489.

Gould et al., "Antischizophrenic Drugs of the Diphenylbutylpiperidine Type Act as Calcium Channel Antagonists," Proc Natl Acad Sci (1983) 80:5122–5125.

Grantham et al., "Fluspirilene Block of N–Type Calcium Current in NGF–Differentiated PC12 Cells," Brit J Pharmacol (1994) 111:438–488.

Ito et al., "U–92032, a T–Type $Ca^{2+}$ Channel Blocker and Antioxidant, Reduces Neuronal Ischemic Injuries," Eur J Pharmacol (1994) 257:203–210.

King et al., "Substituted Diphenylbutylpiperidines Bind to a Uniquue High Affinity Site on the L–Type Calcium Channel," J Biol Chem (1989) 264:5633–5641.

Lee et al., "Cloning and Expression of a Novel Member of the Low Voltage–Activated T–Type Calcium Channel Family," Journal of Neuroscience (1999) 19:1912–1921.

Lehmann et al., "Zur Struktur und Pharmakologies γ–lactonverbruckter Diphenylalkylamine," Arch Pharm (1988) 321:807–812.

McCleskey et al., "Functional Properties of Voltage Dependent Calcium Channels," Curr Topics Membr (1991) 39:295–326.

Miyano et al., "The Synthesis and Antilipidperoxidation Activity of 4,4–diarylbutylamines and 4,4–diarylbutanamides," Chem Pharm Bull (1990) 38(6):1570–1574.

Ohtaka et al., "Benzylpiperazine Derivatives. IV. Syntheses and Cerebral Vasodilating Activities of 1–Benzyl–4–diphenylmethyl–piperazine Derivatives," Chem Pharm Bull (1987) 35(8):3270–3275.

Ohtaka et al., "Benzylpiperazine Derivatives. V. Quantitative Structure–Activity Relationships of 1–Benzyl–4–diphenylmethylpiperazine Derivatives for Cerebral Vasodilating Activity," Chem Pharm Bull (1987) 35(10):4117–4123.

Perez–Reyes et al., "Molecular Characterization of a Neuronal Low–Voltage–Activated T–Type Calcium Channel," Nature (1998)391:896–900.

Prasad et al., "Potential Antihypertensive Agents. II. Unsymmetrically 1.4–disubstituted Piperazines," J Med Chem (1968) 11(6):1144–1150.

Sather et al., "Distinctive Biophysical and Pharmacological Properties of Class A (BI) Calcium Channel $α_1$ Subunits," Neuron (1993) 11:291–303.

Stea et al., "Localization and Functional Properties of a Rat Brain $α_{1A}$ Calcium Channel Reflect Similarities to Neuronal Q–and P–Type Channels," Proc Natl Acad Sci USA (1994) 91:10576–10580.

Stea et al., Handbook of Receptors and Channels (North, R.A. ed. CRC Press 1995) 113–151.

Tytgat et al., "Flunarizine Inhibits a High–threshold Inactivating Calcium Channel (N–type) in Isolated Hippocampal Neurons," Brain Research (1991) 549:112–117.

Uneyama et al., "Non–L–type Actions of Organic $Ca^{2+}$ Channel Blockers: Implications for $Na^+$ and N–type $Ca^{2+}$ Channels Blockades," Calcium Ion Modulators, Sel Pap Satell Symp (1988) 13–23.

Vadodaria et al., "Synthesis and Central Nervous System Depressant Activity of New Piperazine Derivatives and Related Compounds. II,"J Med Chem (1969) 12:860–865.

Zikolova et al., "Analogs of 1N–benzhydryl–4N–cinnamylpiperazine (cinnarizine). V. New N1–benzhydryl–N4–substituted Piperazines," Tr Nauchnoizsled Khim—Farm Inst (1984) 14:23–28 (Database Chemabs Online! Chemical Abstracts Service, Columbus, Ohio, AN: 103:37454, XP002133053).

Zikolova et al., "Analogs of N1–benzhydryl–N4–cinnamylpiperazine (cinnarizine). II. N1–substituted–N4–benzhydrylpiperazines," Tr Nauchnoizsled Khim—Farm Inst (1972) 8:59–67 (Database Chemabs Online! Chemical Abstracts Service, Columbus, Ohio, AN: 78:147908, ZP0021330454).

* cited by examiner

PARTIALLY SATURATED CALCIUM CHANNEL BLOCKERS

This application is a continuation of U.S. Ser. No. 09/476,929 filed Dec. 30, 1999, now abandoned which is a continuation-in-part of U.S. Ser. No. 09/401,699, filed Sep. 23, 1999, now U.S. Pat. No. 6,294,533 which is a continuation-in-part of U.S. Ser. No. 09/107,037 filed Jun. 30, 1998, now U.S. Pat. No. 6,011,035. This Application also claim priority to U.S. Provisional Application No. 60/172,765 filed Dec. 20, 1999. The contents of all applications are incorporated herein by reference.

TECHNICAL FIELD

The invention relates to compounds useful in treating conditions associated with calcium channel function. More specifically, the invention concerns compounds containing benzhydril and 6-membered heterocyclic moieties that are useful in treatment of conditions such as stroke and pain.

BACKGROUND ART

Native calcium channels have been classified by their electrophysiological and pharmacological properties as T, L, N, P and Q types (for reviews see McCleskey, E. W. et al. *Curr Topics Membr* (1991) 39:295–326, and Dunlap, K. et al. *Trends Neurosci* (1995) 18:89–98). T-type (or low voltage-activated) channels describe a broad class of molecules that transiently activate at negative potentials and are highly sensitive to changes in resting potential. The L, N, P and Q-type channels activate at more positive potentials (high voltage activated) and display diverse kinetics and voltage-dependent properties. There is some overlap in biophysical properties of the high voltage-activated channels, consequently pharmacological profiles are useful to further distinguish them. L-type channels are sensitive to dihydropyridine agonists and antagonists, N-type channels are blocked by the *Conus geographus* peptide toxin, ω-conotoxin GVIA, and P-type channels are blocked by the peptide ω-agatoxin IVA from the venom of the funnel web spider, *Agelenopsis aperta*. A fourth type of high voltage-activated calcium channel (Q-type) has been described, although whether the Q- and P-type channels are distinct molecular entities is controversial (Sather, W. A. et al. *Neuron* (1995) 11:291–303; Stea, A. et al. *Proc Natl Acad Sci USA* (1994) 91:10576–10580; Bourinet, E. et al. *Nature Neuroscience* (1999) 2:407–415). Several types of calcium conductances do not fall neatly into any of the above categories and there is variability of properties even within a category suggesting that additional calcium channels subtypes remain to be classified.

Biochemical analyses show that neuronal high voltage activated calcium channels are heterooligomeric complexes consisting of three distinct subunits ($\alpha_1$, $\alpha_2\delta$ and $\beta$) (reviewed by De Waard, M. et al. *Ion Channels* (1997) vol. 4, Narahashi, T. ed. Plenum Press, NY). The $\alpha_1$ subunit is the major pore-forming subunit and contains the voltage sensor and binding sites for calcium channel antagonists. The mainly extracellular $\alpha_2$ is disulfide-linked to the transmembrane $\delta$ subunit and both are derived from the same gene and are proteolytically cleaved in vivo. The $\beta$ subunit is a nonglycosylated, hydrophilic protein with a high affinity of binding to a cytoplasmic region of the $\alpha_1$ subunit. A fourth subunit, $\gamma$, is unique to L-type calcium channels expressed in skeletal muscle T-tubules. The isolation and characterization of $\gamma$-subunit-encoding cDNAs is described in U.S. Pat. No. 5,386,025 which is incorporated herein by reference.

Recently, each of these $\alpha_1$ subtypes has been cloned and expressed, thus permitting more extensive pharmacological studies. These channels have been designated $\alpha_{1A}$–$\alpha_{1I}$ and $\alpha_{1S}$ and correlated with the subtypes set forth above. $\alpha_{1A}$ channels are of the P/Q type; $\alpha_{1B}$ represents N; $\alpha_{1C}$, $\alpha'_{1D}$, $\alpha_{1F}$ and $\alpha_{1S}$ represent L; $\alpha_{1E}$ represents a novel type of calcium conductance, and $\alpha_{1G}$–$\alpha_{1I}$ represent members of the T-type family, reviewed in Stea, A. et al. in Handbook of Receptors and Channels (1994), North, R. A. ed. CRC Press; Perez-Reyes, et al. *Nature* (1998) 391:896–900; Cribbs, L. L. et al. *Circulation Research* (1998) 83:103–109; Lee, J. H. et al. *Journal of Neuroscience* (1999) 19:1912–1921.

Further details concerning the function of N-type channels, which are synaptic channels, have been disclosed, for example, in U.S. Pat. No. 5,623,051, the disclosure of which is incorporated herein by reference. As described, N-type channels possess a site for binding syntaxin, a protein anchored in the presynaptic membrane. Blocking this interaction also blocks the presynaptic response to calcium influx. Thus, compounds that block the interaction between syntaxin and this binding site would be useful in neural protection and analgesia. Such compounds have the added advantage of enhanced specificity for presynaptic calcium channel effects.

U.S. Pat. No. 5,646,149 describes calcium channel antagonists of the formula A-Y-B wherein B contains a piperazine or piperidine ring directly linked to Y. An essential component of these molecules is represented by A, which must be an antioxidant; the piperazine or piperidine itself is said to be important. The exemplified compounds contain a benzhydril substituent, based on known calcium channel blockers (see below). U.S. Pat. No. 5,703,071 discloses compounds said to be useful in treating ischemic diseases. A mandatory portion of the molecule is a tropolone residue; among the substituents permitted are piperazine derivatives, including their benzhydril derivatives. U.S. Pat. No. 5,428,038 discloses compounds which are said to exert a neural protective and antiallergic effect. These compounds are coumarin derivatives which may include derivatives of piperazine and other six-membered heterocycles. A permitted substituent on the heterocycle is diphenylhydroxymethyl. Thus, approaches in the art for various indications which may involve calcium channel blocking activity have employed compounds which incidentally contain piperidine or piperazine moieties substituted with benzhydril but mandate additional substituents to maintain functionality.

Certain compounds containing both benzhydril moieties and piperidine or piperazine are known to be calcium channel antagonists and neuroleptic drugs. For example, Gould, R. J. et al. *Proc Natl Acad Sci USA* (1983) 80:5122–5125 describes antischizophrenic neuroleptic drugs such as lidoflazine, fluspirilene, pimozide, clopimozide, and penfluridol. It has also been shown that fluspirilene binds to sites on L-type calcium channels (King, V. K. et al. *J Biol Chem* (1989) 264:5633–5641) as well as blocking N-type calcium current (Grantham, C. J. et al. *Brit J Pharmacol* (1944) 111:483–488). In addition, Lomerizine, developed by Kanebo KK, is a known non-specific calcium channel blocker. A review of publications concerning Lomerizine is found in Dooley, D., *Current Opinion in CPNS Investigational Drugs* (1999) 1:116–125.

U.S. application Ser. No. 09/401,699 filed Sep. 23, 1999 and incorporated herein by reference discloses benzhydril-substituted piperidines and piperazines which block calcium channels, especially N-type channels.

The present invention is based on the recognition that compounds comprising a six-membered heterocyclic ring containing at least one nitrogen coupled to two hydrophobic clusters (each cluster coupled optionally through a linker) provide calcium channel blocking activity. Thus these compounds are particularly useful for treating stroke and pain. By focusing on these moieties, compounds useful in treating indications associated with excessive calcium channel activity and combinatorial libraries that contain these compounds can be prepared.

DISCLOSURE OF THE INVENTION

The invention relates to compounds useful in treating conditions such as stroke, migraine, chronic neuropathic and acute pain, epilepsy, hypertension, cardiac arrhythmias, and other indications associated with calcium metabolism, including synaptic calcium channel-mediated functions. The compounds of the invention are derivatives of piperidine or piperazine linked to hydrophobic substituents which enhance the calcium channel blocking activity. Thus, in one aspect, the invention is directed to therapeutic methods that employ compounds of the formulas

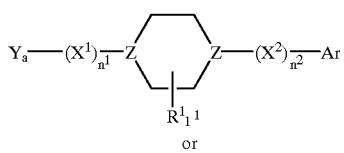

(1a)

or

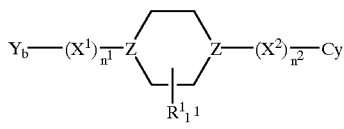

(1b)

wherein each Z is independently N or CH, but one Z must be N;

wherein $n^1$ is 1 and n is 0 or 1;

$X^1$ and $X^2$ are linkers;

Ar represents one or two substituted or unsubstituted aromatic or heteroaromatic rings, and Cy represents one or two substituted or unsubstituted aliphatic cyclic or heterocyclic rings, or consists of one substituted or unsubstituted aliphatic cyclic or heterocyclic ring and one substituted or unsubstituted aromatic or heteroaromatic ring;

each of $Y_a$ and $Y_b$ is two substituted or unsubstituted aromatic or heteroaromatic rings, or can be two substituted or unsubstituted aliphatic cyclic or heterocyclic rings or consists of one substituted or unsubstituted aliphatic cyclic or heterocyclic ring and one substituted or unsubstituted aromatic or heteroaromatic ring;

with the proviso that said rings cannot both be phenyl when both Ar includes a single phenyl ring and $X^1$ contains less than 5C;

and with the proviso that formula (1b) must contain at least one aromatic or heteroaromatic ring;

$1^1$ is 0 or 1;

$R^1$ is substituted or unsubstituted alkyl (1–6C), substituted or unsubstituted aryl (6–10C) or substituted or unsubstituted arylalkyl (7–16C) optionally containing 1–4 heteroatoms selected from the group consisting of halo, N, P, O, and S or may independently be halo, OR, SR, $NR_2$, OOCR, NROCR, COR, COOR, $CONR_2$, $CF_3$, CN or $NO_2$, wherein R is H or alkyl (1–6C).

Substituents included in $Y_a$, $Y_b$, Ar and Cy are also selected from the foregoing.

The invention is directed to methods to antagonize calcium channel activity using the compounds of formulas (1a) or (1b) and thus to treat associated conditions. It will be noted that the conditions may be associated with abnormal calcium channel activity, or the subject may have normal calcium channel function which nevertheless results in an undesirable physical or metabolic state that can be benefited by lowering calcium transport. In another aspect, the invention is directed to pharmaceutical compositions containing these compounds.

The invention is also directed to combinatorial libraries containing the compounds of formulas (1a) or (1b) and to methods to screen these libraries for members containing particularly potent calcium channel blocking activity including blocking activity for channels of a particular type.

MODES OF CARRYING OUT THE INVENTION

The compounds of formulas (1a) or (1b), useful in the methods of the invention, exert their desirable effects through their ability to antagonize the activity of calcium channels, including those which are synaptic in their activity. While the compounds of formulas (1a) or (1b) generally have this activity, the availability of a multiplicity of calcium channel blockers permits a nuanced selection of compounds for particular disorders. Thus, the availability of this class of compounds provides not only a genus of general utility in indications that are affected by excessive calcium channel activity, but also provides a large number of compounds which can be mined and manipulated for specific interaction with particular forms of calcium channels. The availability of recombinantly produced calcium channels of the $\alpha_{1A}$–$\alpha_{1I}$ and $\alpha_{1S}$ types set forth above, facilitates this selection process. Dubel, S. J. et al. *Proc Natl Acad Sci USA* (1992) 89:5058–5062; Fujita, Y. et al. *Neuron* (1993) 10:585–598; Mikami, A. et al. *Nature* (1989) 340:230–233; Mori, Y. et al. *Nature* (1991) 350:398–402; Snutch, T. P. et al. *Neuron* (1991) 7:45–57; Soong, T. W. et al. *Science* (1993) 260:1133–1136; Tomlinson, W. J. et al *Neuropharmacology* (1993) 32:1117–1126; Williams, M. E. et al. *Neuron* (1992) 8:71–84; Williams, M. E. et al. *Science* (1992) 257:389–395; Perez-Reyes, et al. *Nature* (1998) 391:896–900; Cribbs, L. L. et al. *Circulation Research* (1998) 83:103–109; Lee, J. H. et al. *Journal of Neuroscience* (1999) 19:1912–1921.

Thus, while it is known that calcium channel activity is involved in a multiplicity of disorders, the types of channels associated with particular conditions is the subject of ongoing data collection. The association of N-type channels in conditions associated with neural transmission would indicate that compounds of the invention which target N-type receptors are most useful in these conditions. Most of the members of the genus of compounds of formulas (1a) or (1b) target N-type channels; other members of the genus may target other channels; many members of the genus target channels of several types.

There are two distinguishable types of calcium channel inhibition. The first, designated "open channel blockage," is conveniently demonstrated when displayed calcium channels are maintained at an artificially negative resting potential of 3 about –100 mV (as distinguished from the typical endogenous resting maintained potential of about –70 mV). When the displayed channels are abruptly depolarized under these conditions, calcium ions are caused to flow through the channel and exhibit a peak current flow which then decays. Open channel blocking inhibitors diminish the current exhibited at the peak flow and can also accelerate the rate of current decay.

This type of inhibition is distinguished from a second type of block, referred to herein as "inactivation inhibition." When maintained at less negative resting potentials, such as the physiologically important potential of −70 mV, a certain percentage of the channels may undergo conformational change, rendering them incapable of being activated—i.e., opened—by the abrupt depolarization. Thus, the peak current due to calcium ion flow will be diminished not because the open channel is blocked, but because some of the channels are unavailable for opening (inactivated). "Inactivation" type inhibitors increase the percentage of channels that are in an inactivated state.

Among the conditions associated in which blocking calcium transport would be of therapeutic value are stroke, head trauma, epilepsy, and chronic, neuropathic and acute pain. Calcium transport, especially that associated with N-type channels, is also implicated in other neurological disorders such as migraine, epilepsy, mood disorders, schizophrenia, and certain degenerative disorders. Other conditions that benefit from reduced calcium flux include depression, anxiety, and other psychoses. Cardiovascular conditions benefited include hypertension and cardiac arrhythmias.

The availability of the libraries containing the compounds of formulas (1a) or (1b) also provides a source of compounds which may be screened for activity with regard to the various ion channels. The various types of ion channels are associated with conditions that are susceptible to treatment. Blockers of sodium channels, for example, are useful as local anesthetics, and in treating cardiac arrhythmias, as anticonvulsants, and in treating hyperkalemic periodic paralysis. Potassium channel blockers are useful in treating hypertension and cardiac arrhythmias; various other receptors are associated with psychoses, schizophrenia, depression, and apnea. Thus, the library of compounds of the invention is useful in standard screening techniques as a source of effective pharmaceutical compounds.

Synthesis

The compounds of the invention may be synthesized using conventional methods. Illustrative of such methods are the following schemes.

The piperazine derivatives of the invention are prepared conveniently by synthetic routes wherein one of the linkers, $X^1$ or $X^2$, is supplied as a carboxylic acid or carboxylic acid derivative and is coupled to piperazine already bound to the remaining substituent. Thus, in general, these compounds are prepared by Reaction Scheme 1 illustrated below for the embodiment wherein Ar is benzhydril and $Y_a(X^1)_{n1}$ is depicted as R.

Scheme 1

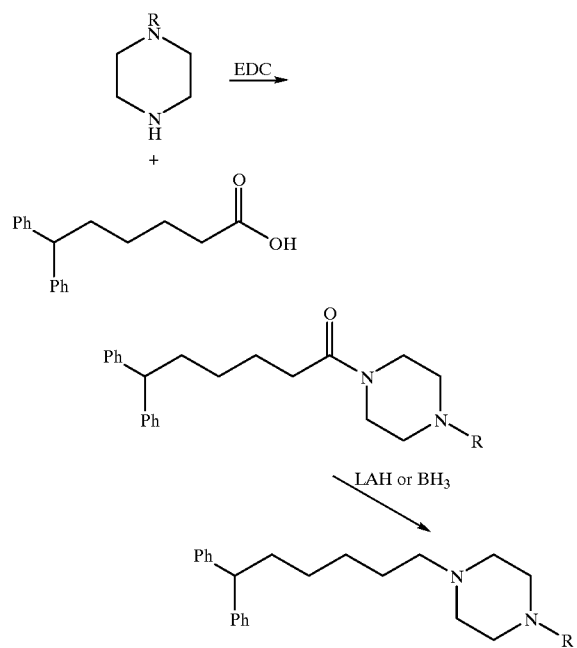

The intermediate amide product can be reduced as shown, if desired, using a suitable reducing agent. Preferably, the reducing agent is $BH_3$ if R represents phenyl or benzyl, or is LAH if R contains a π-bond other than in an aromatic system, such as the instance wherein R is —$CH_2CH$=$CH\phi$. Alternatively, the piperazine ring nitrogen shown coupled to R is protected with t-butyl carbonate (BOC) which can then be removed and replaced with a different substituent as shown in Reaction Scheme 2 and then reduced, for example, with $BH_3$.

Reaction Scheme 2

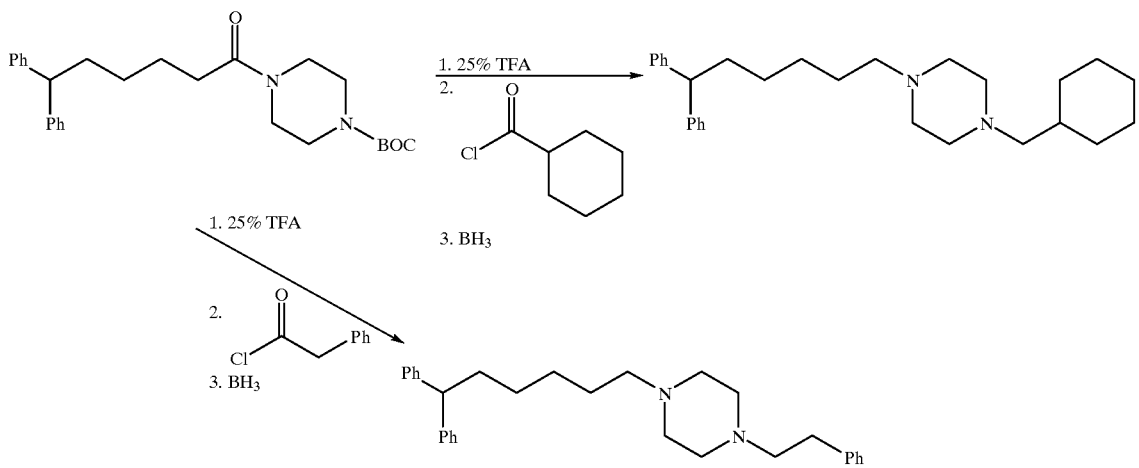

In the foregoing reaction schemes, EDC represents ethyldicyclohexylcarbodiimide, LAH represents lithium aluminum hydride, TFA is trifluoroacetic acid.

Some of the desired carboxylates are commercially available including instances which include cyclic aliphatics. Where they are not, they can be prepared by a Wittig reaction and reduced as desired, as shown in Reaction Scheme 3, which illustrates preparation of the benzhydril embodiment using benzophenone. However, phenylcyclohexylketone or dicyclohexylketone can be substituted for benzophenone to obtain the corresponding embodiments wherein the substituent coupled to linker is symbolized by Cy in formula (1b).

Reaction Scheme 3

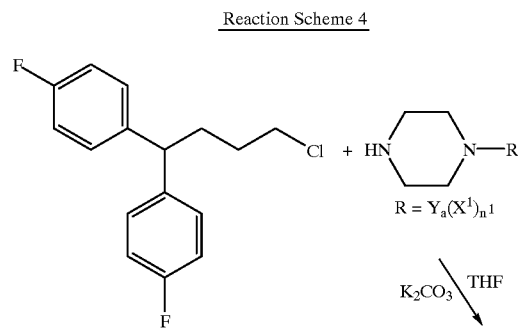

In this reaction scheme, LiHMDS represents lithium hexamethyl disilazide. The reaction proceeds smoothly with benzophenone and phenylcyclohexylketone; use of dicyclohexylketone results in an aberrant molecular weight as measured by mass spectrometry, but nevertheless provides product.

The reagents in the above-referenced scheme may or may not contain substitutions on the aromatic or cyclic aliphatic moieties. For example, compounds in the bis-4-fluorophenyl butylidine series are commercially available and Reaction Scheme 4 illustrates the preparation of these compounds.

Reaction Scheme 4

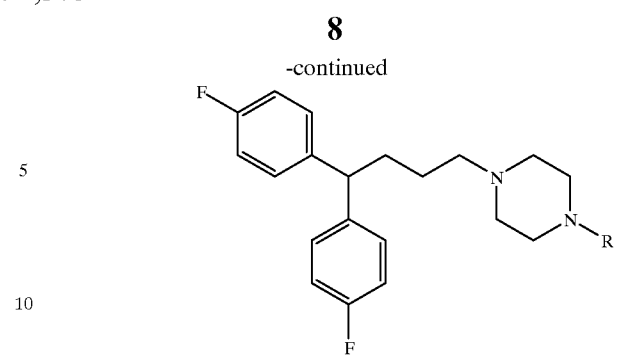

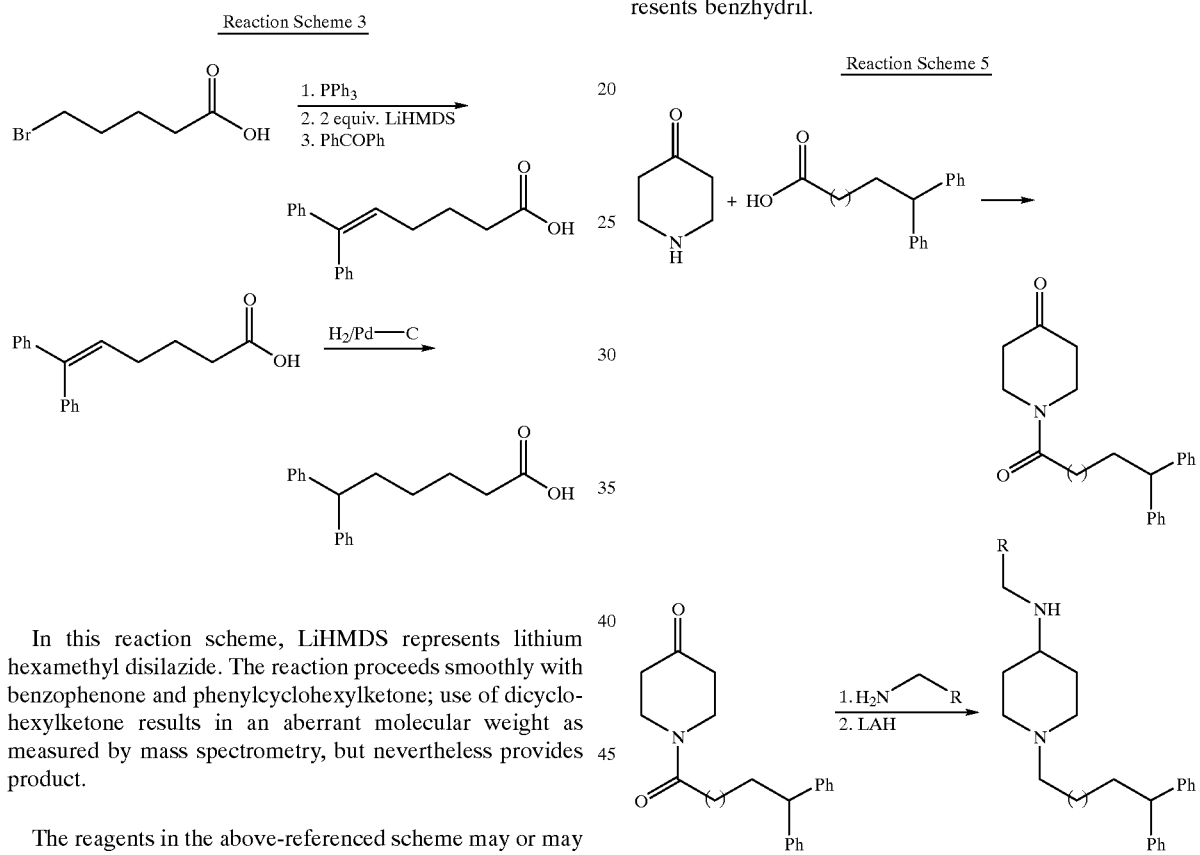

The compounds of the invention that are piperidine derivatives are prepared in an analogous manner, as shown in Reaction Scheme 5 using the illustration where Ar represents benzhydril.

Reaction Scheme 5

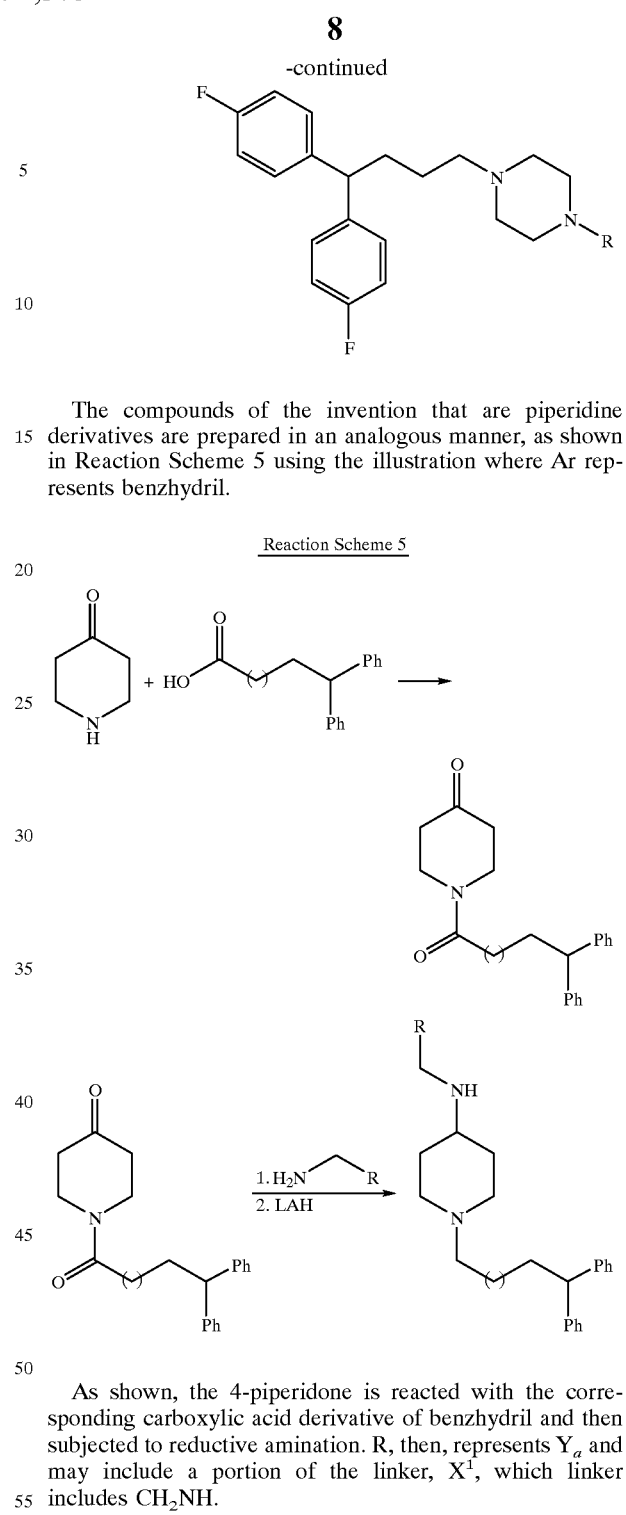

As shown, the 4-piperidone is reacted with the corresponding carboxylic acid derivative of benzhydril and then subjected to reductive amination. R, then, represents $Y_a$ and may include a portion of the linker, $X^1$, which linker includes $CH_2NH$.

In general, the synthesis of the compounds of the invention is conventional and employs techniques generally known in the art.

The compounds of formulas (1a) or (1b) are defined as shown in terms of the embodiments of their various substituents:

each Z is independently N or CH, but one Z must be N.

$R^1$ is alkyl (1–6C) aryl (6–10C) or arylalkyl (7–16C) optionally containing 1–4 heteroatoms selected from the group consisting of N, P, O, S, and halo. $R^1$ may also be the "substituents" halo, OR, SR, $NR_2$, OOCR, NROCR, COR, COOR, $CONR_2$, $CF_3$, CN or $NO_2$, wherein R is H or alkyl (1–6C). These "substituents" may also be present on the alkyl, aryl or arylalkyl moieties contained in Formulas 1a and 1b; aryl groups may also contain alkyl substituents. Preferred embodiments of $R^1$ include phenyl, phenylalkyl, F, Cl, Br, I, $CF_3$, OR, $NR_2$ and alkyl. Particularly preferred are F, OMe, $NH_2$, $NMe_2$, NHOAc, $CONH_2$, Br, COOEt, and COOMe, as well as methyl. Preferably, however, $1^1$ is 0.

As $n^2$ may be 0 or 1, $X^2$ may be present or not. $X^1$ and $X^2$ are suitable linkers containing 1–10C which may be saturated or unsaturated and may contain a ring. The linker may also contain one or two heteroatoms selected from N, O and S and may be substituted with the "substituents" listed above. Preferred embodiments of $X^2$ include —$(CH_2)_a$— wherein a is 1–10, preferably 1–6, —$(CH_2)_b CO$—, where b is 1–9, and —$(CH_2)_c CH=CH$, where c is 0–4. Also preferred for $X^2$ is —$NH(CH_2)_d$— where d is 1–6, when the coupled Z is CH.

Thus, formulas (1a) and (1b) are similar, except that compounds of formula (1a) contain more mandated aromatic substituents linked to the heterocyclic 6-membered ring and those of (1b) contain more aliphatic cyclic or heterocyclic moieties. In each case, when $X^2$ is present, $X^2$ represents a linker which spaces the Ar or Cy moiety from Z preferably at a distance of 3–20 Å, and may contain at least one heteroatom which is nitrogen or oxygen. Included in such linkers are amines and carbonyl functionalities, including amides. The linker may also be unsaturated or may be an alkylene group. Typically, $X^2$ is $(CH_2)_{1-8}$ or —NH$(CH_2)_{1-6}$— or $(CH_2)_{0-5}$, or —$CH=CH$—$(CH_2)_{0-3}$— or —$CO(CH_2)_{1-8}$—. Similarly, $X^1$ spaces the $Y_a$ or $Y_b$ from the nitrogen of the heterocyclic ring at a distance of 3–20 Å.

In both cases, when linked to two aromatic or heterocyclic or other cyclic moieties, as is always the case for $Y_a$ and $Y_b$, $X^1$ or $X^2$ must accommodate this and a typical embodiment is —$(CH_2)_{0-6}$—CH—$CH(CH_2)_{0-6}CO$, or —$CH(CH_2)_{0-7}$. $X^1$ or $X^2$ may also contain a π-bond, e.g., —$(CH_2)_{0-5}CH=C$, thus providing sufficient valence to couple two ring systems or $C=CH(CH_2)_{0-5}$—.

In preferred forms of formulas (1a) and (1b), $X^2$ is $(CH_2)_{1-8}$, $(CH_2)_{1-5}CO(CH_2)_{0-3}$, $(CH_2)_{1-5}NH(CH_2)_{0-3}$, $(CH_2)_{0-5}CONH(CH_2)_{0-3}$, —$(CH_2)_{0-5}CH=CH(CH_2)_{0-3}$— and $(CH_2)_{1-5}NHCO(CH_2)_{0-3}$, with accommodation as required for two rings. Preferred for $X^1$ are $CH(CH_2)_{1-10}$ and $CH(CH_2)_{1-9}CO$.

It is believed that halogenation of the compounds of the invention is helpful in modulating the in vivo half-life, and it may be advantageous to include halogen-substituted rings in the compounds. Indeed, various substituents may thus be included. These substituents include alkyl (1–6C), aryl (6–10C) or arylalkyl (7–16C) optionally containing 1–4 heteroatoms selected from the group consisting of halo, N, P, O, and S or may be the "substituents" halo, OR, SR, $NR_2$, OOCR, NROCR, COR, COOR, $CONR_2$, $CF_3$, CN or $NO_2$, wherein R is H or alkyl (1–6C). These substituents may also be present on the alkyl, aryl or arylalkyl or other cyclic moieties; aryl or other cyclic moieties groups may also contain alkyl substituents.

Typical heteroaromatic moieties include pyridyl, pyrimidyl, quinolyl and the like. Typical aliphatic heterocycles include, for example, piperidinyl, piperazinyl, tetrahydrofuranyl, pyranyl, and the like. Preferred embodiments of $Y_a$ and $Y_b$ include two cyclohexyl residues or a cyclohexyl and a phenyl residue.

Thus, all of the foregoing aromatic, heteroaromatic, cyclic aliphatic, and heterocyclic aliphatic moieties may be substituted or unsubstituted. Typical "substituents" include halo, OR, SR, $NR_2$, OOCR, NROCR, COR, COOR, $CONR_2$, $CF_3$, CN or $NO_2$, wherein R is H or alkyl (1–6C). They may also be substituted by alkyl (1–6C), aryl (6–10C) or arylalkyl (7–16C) optionally containing 1–4 heteroatoms selected from the group consisting of halo, N, P, O, and S which may themselves contain "substituents." Aryl residues or other cyclic residues may also be substituted by alkyl.

Preferred substituents include halo, $CF_3$, OR, $NR_2$, $COONR_2$, COOR, and the like.

In the compounds of formula (1a), preferred embodiments of Ar include two phenyl moieties or a single phenyl moiety. In compounds of formula (1b), preferred embodiments of Cy include a single cyclohexyl, a cyclohexyl and phenyl moiety, or two cyclohexyl moieties.

In one set of preferred embodiments of Formula 1a $Y_a$ is two substituted or unsubstituted phenyl, X' is $CH(CH_2)_5$ or $CH(CH_2)_4 CO$, Z is N, and $X^2$ is $CH_2$ and $n^2$ is 0 or 1. In this embodiment, Ar is preferably an optionally substituted ring which is phenyl, pyrimidyl, especially 2-pyrimidyl or pyridyl, especially 2-pyridyl.

The invention compounds may also be supplied as pharmaceutically acceptable salts. Pharmaceutically acceptable salts include the acid addition salts which can be formed from inorganic acids such as hydrochloric, sulfuric, and phosphoric acid or from organic acids such as acetic, propionic, glutamic, glutaric, as well as acid ion-exchange resins. If the compounds contain carboxyl groups, the salts of the carboxyl groups may also be included. typical pharmaceutically acceptable salts are sodium, potassium, or calcium salts if appropriate, or salts with inorganic bases such as caffeine.

Utility and Administration

For use as treatment of human and animal subjects, the compounds of the invention can be formulated as pharmaceutical or veterinary compositions. Depending on the subject to be treated, the mode of administration, and the type of treatment desired—e.g., prevention, prophylaxis, therapy; the compounds are formulated in ways consonant with these parameters. A summary of such techniques is found in Remington's *Pharmaceutical Sciences*, latest edition, Mack Publishing Co., Easton, Pa., incorporated herein by reference.

In general, for use in treatment, the compounds of formulas (1a) and (1b) may be used alone, as mixtures of two or more compounds of formulas (1a) and (1b) or in combination with other pharmaceuticals. Depending on the mode of administration, the compounds will be formulated into suitable compositions to permit facile delivery.

Formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. The formulation will generally include a diluent as well as, in some cases, adjuvants, buffers, preservatives and the like. The compounds can be administered also in liposomal compositions or as microemulsions.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised. See, for example, U.S. Pat. No. 5,624,677.

Systemic administration may also include relatively non-invasive methods such as the use of suppositories, transdermal patches, transmucosal delivery and intranasal administration. Oral administration is also suitable for compounds of the invention. Suitable forms include syrups, capsules, tablets, as in understood in the art.

For administration to animal or human subjects, the dosage of the compounds of the invention is typically 0.1–15 mg/kg, preferably 0.1–1 mg/kg. However, dosage levels are highly dependent on the nature of the condition, the condition of the patient, the judgment of the practitioner, and the frequency and mode of administration.

Screening Methods

The compounds of the invention can be synthesized individually using methods known in the art per se, or as members of a combinatorial library. In general, $Y_a$ or $Y_b$ is coupled, along with any linking moiety, to the nitrogen of the piperazine or piperidine ring. This ring itself is generally appropriately substituted with $(X^2)_n$—Ar or $(X^2)_n$—Cy prior to this coupling. Typically, $Y_a(X^1)_{n1}$ or $Y_b(X^1)_{n1}$ is supplied containing a suitable electron-withdrawing leaving group, thus effecting the coupling to the ring nitrogen.

Synthesis of combinatorial libraries is now commonplace in the art. Suitable descriptions of such syntheses are found, for example, in Wentworth, Jr., P. et al. *Current Opinion in Biol* (1993) 9:109–115; Salemme, F. R. et al. *Structure* (1997) 5:319–324. The libraries contain compounds with various embodiments of $R^1$, $X^1$, $X^2$, Ar, Cy, Y and Z, along with appropriate substituents. These libraries, which contain, as few as 10, but typically several hundred members to several thousand members, may then be screened for compounds which are particularly effective against a specific subtype of calcium channel. In addition, using standard screening protocols, the libraries may be screened for compounds which block additional channels such as sodium channels, potassium channels and the like.

Methods of performing these screening functions are well known in the art. Typically, the channel to be targeted is expressed at the surface of a recombinant host cell such as human embryonic kidney cells. The ability of the members of the library to bind the channel is measured, for example, by the ability of the compound in the library to displace a labeled binding ligand such as the ligand normally associated with the channel or an antibody to the channel. More typically, ability to antagonize the channel is measured in the presence of the appropriate agonist and the ability of the compound to interfere with the signal generated is measured using standard techniques.

In more detail, one method involves the binding of radiolabeled agents that interact with the calcium channel and subsequent analysis of equilibrium binding measurements including, but not limited to, on rates, off rates, $K_d$ values and competitive binding by other molecules. Another method involves the screening for the effects of compounds by electrophysiological assay whereby individual cells are impaled with a microelectrode and currents through the calcium channel are recorded before and after application of the compound of interest. Another method, high-throughput spectrophotometric assay, utilizes loading of the cell lines with a fluorescent dye sensitive to intracellular calcium concentration and subsequent examination of the effects of compounds on the ability of depolarization by potassium chloride or other means to alter intracellular calcium levels.

The following examples are intended to illustrate but not to limit the invention.

EXAMPLE 1

Assay of N-Type Calcium Channel Blocking Activity

Antagonist activity was measured using whole cell patch recordings on human embryonic kidney cells either stably or transiently expressing rat $\alpha_{1B}+\alpha_{2b}+\beta_{1b}$ channels with 5 mM barium as a charge carrier.

For transient expression, host cells, such as human embryonic kidney cells, HEK 293 (ATCC# CRL 1573) are grown in standard DMEM medium supplemented with 2 mM glutamine and 10% fetal bovine serum. HEK 293 cells are transfected by a standard calcium-phosphate-DNA coprecipitation method using the rat $\alpha_{1B}+\beta_{1b}+\alpha_2\delta$ N-type calcium channel subunits in a vertebrate expression vector (for example, see *Current Protocols in Molecular Biology*).

After an incubation period of from 24 to 72 hrs the culture medium is removed and replaced with external recording solution (see below). Whole cell patch clamp experiments are performed using an Axopatch 200B amplifier (Axon Instruments, Burlingame, Calif.) linked to an IBM compatible personal computer equipped with pCLAMP software. Borosilicate glass patch pipettes (Sutter Instrument Co., Novato, Calif.) were polished (Microforge, Narishige, Japan) to a resistance of about 4 MΩ when filled with cesium methanesulfonate internal solution (composition in MM: 109 $CsCH_3SO_4$, 4 $MgCl_2$, 9 EGTA, 9 HEPES, pH 7.2). Cells were bathed in 5 mM $Ba^{++}$ (in mM: 5 $BaCl_2$, 1 $MgCl_2$, 10 HEPES, 40 tetraethylammonium chloride, 10 glucose, 87.5 CsCl pH 7.2). Current data shown were elicited by a train of 100 ms test pulses at 0.066 Hz from –100 mV and/or –80 mV to various potentials (min. –20 mV, max. +30 mV). Drugs were perfused directly into the vicinity of the cells using a microperfusion system.

Normalized dose-response curves were fit (Sigmaplot 4.0, SPSS Inc., Chicago, Ill.) by the Hill equation to determine $IC_{50}$ values. Steady-state inactivation curves were plotted as the normalized test pulse amplitude following 5 s inactivating prepulses at +10 mV increments. Inactivation curves were fit (Sigmaplot 4.0) with the Boltzman equation, $I_{peak}$ (normalized)=$1/(1+\exp((V-V_h)z/25.6))$, where V and $V_h$ are the conditioning and half inactivation potentials, respectively, and z is the slope factor.

EXAMPLE 2

Synthesis of Illustrative Compounds of Formula (1a)

A. Preparation of $ArX^2$.

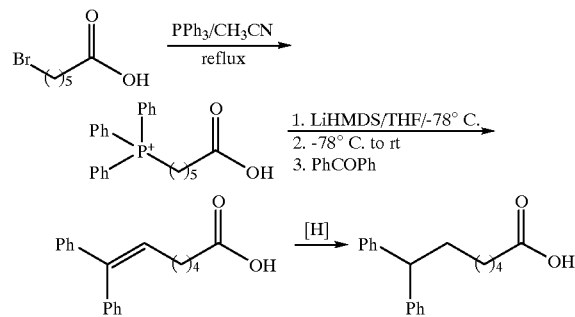

6-Bromohexanoic acid (7.08 g, 36.3 mM) and triphenylphosphine (10 g, 38.2 mM) was mixed in dry $CH_3CN$ (40 ml). The reaction mixture was heated to reflux overnight and allowed to cool to RT. The solution was concentrated under reduced pressure to give a viscous gel. Approximately 75 ml of THF was added to the reaction mixture and the walls of the flask were scratched with a spatula to start crystallization. The resulting solid was filtered under vacuum, washed with THF and dried under reduced pressure and used without further purification. The product from the above reaction (1.5 g) was suspended in dry THF and the flask purged with $N_2$ and cooled to −78° C. To the stirred reaction was added lithium hexamethyldisilazide (LiHMDS) (10 ml, 1 M in THF). The yellow solution was stirred at −78° C. for 1 h over which time the reaction darkened slightly. The cooling bath was removed and the reaction allowed to warm to RT. The reaction was kept at RT for 1 h during which time the solution turned a dark red color and most of the solids went into solution. Benzophenone (0.54 g in 3 ml THF) was added to the reaction and allowed to react overnight. The yellow solution was concentrated under reduced pressure to give a yellow solid. The resulting solid was partitioned between ether and 10% HCl. The organic layer was washed with water (2×) and extracted with 10% NaOH (3×). The combined aqueous base fractions were acidified with conc. HCl to a pH of 4. The water layer was extracted with ether (3×) and the combined organic fractions dried over $Na_2SO_4$. The ether was evaporated to dryness under reduced pressure to give a colorless oil that crystallized on standing to give a waxy solid. NMR and MS showed this material was clean enough to continue without further purification.

The alkene was dissolved in 30 ml MeOH and mixed with 5% Pd—C and placed in a Parr hydrogenator. The reaction vessel was purged with hydrogen and pressurized to 60 PSIG and reacted at RT for 5 h. The reaction mixture was sampled and analyzed by TLC. If the TLC when stained with $KMnO_4$ showed a positive test for alkenes, the reaction mixture was resubjected to the reaction conditions. After the reaction was done the solution was filtered through a plug of celite and the methanol filtrate was concentrated under vacuum.

B. Conversion to Formula(1a)

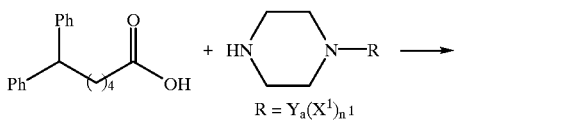

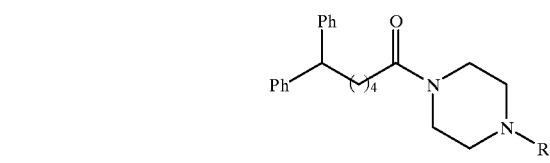

(1) 6,6-Diphenylhexanoic acid (0.4 mM) was mixed with the desired N-substituted piperazine (0.35 mM) in dry THF (7 ml). To each was added EDC (0.5 mM) and DMAP (cat) and the mixture heated to 40° C. with shaking overnight. The reactions were diluted with ethyl acetate and washed with water (4×) and 10% NaOH (3×) and dried over sodium sulphate and evaporated to dryness. The resulting residue was purified by column chromatography (silica gel, 1:1 hexane:EtOAc). The amide products were characterized by HPLC-MS.

(2) the amides resulting from (1) were dissolved in dry THF (5 ml) and reacted with $LiAlH_4$ (1 M in THF) and allowed to react for 6 h. The reactions were quenched with EtOAc (15 ml) and extracted with water (5×) 10% NaOH (10×), brine (1×), dried over sodium sulphate and concentrated under reduced pressure. Most of the products at this stage were >80% pure. Those <80% were purified for running a short column (silica gel, 1:1 hex:EtOAc).

Similarly, the corresponding ω,ω-diphenyl heptanoic, pentanoic, butanoic, propanoic, and acetic acids were mixed with the desired N-substituted piperazine and carried through the reactions scheme shown above to provide the corresponding products.

C. Formula (1a) Through a BOC Intermediate

The reaction set forth in paragraph B(1) above was carried out using BOC-substituted piperazine to obtain the corresponding amide which was then converted to compounds analogous to those of formula (1a) as shown below:

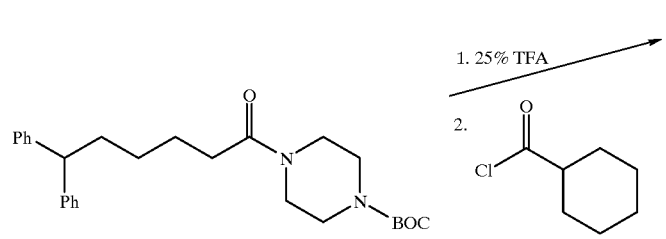

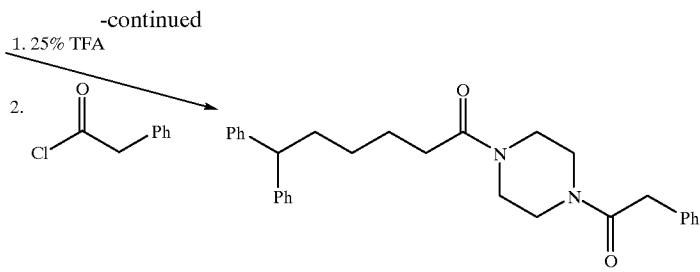

The substituted BOC piperazine (65 mg, 0.15 mM) was dissolved in TFA (25% in $CH_2Cl_2$, 3 ml) in a dry 20 ml vial. The vial was loosely capped to allow for the release of $CO_2$. The mixture was allowed to react for 1 h then concentrated under vacuum. The residue was sampled for MS and showed the molecular ion for the free amine. The residue was redissolved in THF and reacted with cyclohexanecarbonyl chloride (46 mg, 42 µl, 0.31 mM) and DEEA (57 mg, 77.7 µl) and stirred at RT for 2 h. The reaction mixture was diluted with EtOAc and extracted with water (3×), 10% NaOH (6×), 10% HCl (3×), brine (1×) and dried over sodium sulphate. The product was generally clean enough after work up but could be further purified via column (silica gel, 1:1 hex:EtOAc). The procedure for phenylacetyl chloride was the same as for the above.

D. Formula (1a)-Alternative Synthesis

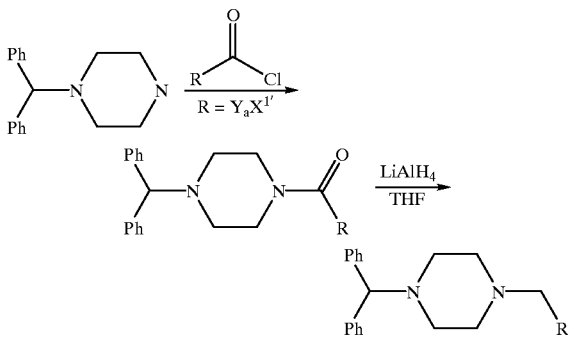

N-(Diphenylmethyl)piperazine (0.5 mM) was dissolved in dry THF (10 ml). To each reaction flask was added powdered $K_2CO_3$ and the corresponding acid chloride ($Y_a$ coupled to $X^1$ which includes CO) (0.7 mM). The reactions were stirred at RT for 2 h and quenched with 105 NaOH (10 ml) and extracted with EtOAc (10 ml). The organic layer was washed with 10% NaOH (4×) and dried over sodium sulphate. The solutions were concentrated and purified by column chromatography (silica gel, 1:1 hex:EtOAc) to give the desired amides.

The above amides were dissolved in dry THF (5 ml) and reacted with $LiAlH_4$ (1M in THF) and allowed to react for 6 h. The reactions were quenched with EtOAc (15 ml) and extracted with water (5×) 10% NaOH (10×), brine (1×), dried over sodium sulphate and concentrated under reduced pressure. Most of the products at this stage were >80% pure. Those <80% were purified by running a short column (silica gel, 1:1 hex:EtOAc).

E. Formula (1a)-Alternative Synthesis

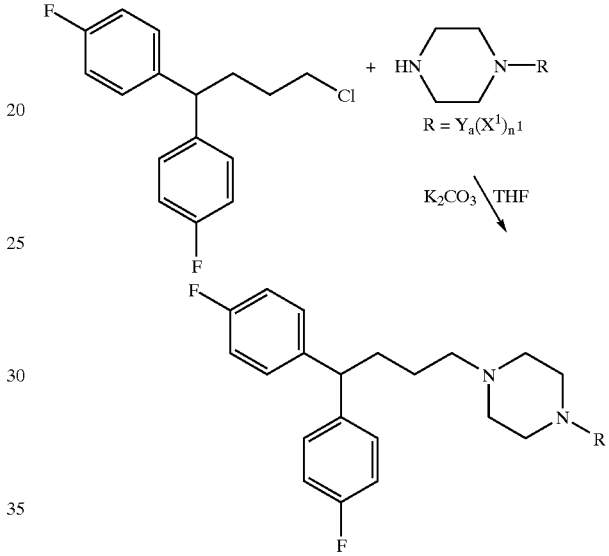

The reagents 1,1'-bis(4-fluorobenzene)-4-chlorobutlidine (1.198 g, 1 ml, 4.25 mM) and the desired substituent piperazine (4.87 mM) was dissolved in dry THF. To each reaction was added ~1 g of powdered $K_2CO_3$ and the reaction stirred at RT overnight. The reaction mixture was diluted with EtOAc and extracted with water (3×), 10% NaOH (3×), brine (1×) and dried over sodium sulphate. The reaction mixtures were then concentrated under reduced pressure and the residue purified via column chromatography.

EXAMPLE 3

Channel Blocking Activities of Various Invention Compounds

Using the procedure set forth in Example 1, various compounds of the invention were tested for their ability to block N-type calcium channels. The results are shown in Tables 1 and 2, where $IC_{50}$ is given in µM (micromolar). In all cases, $1^1$ is 0, both Z are N, both $n^1$ and $n^2$ are 1.

TABLE 1

| Formula (1a): both Z are N; $I^1$ is 0; $n^1$ and $n^2$ are 1 | | | | | |
|---|---|---|---|---|---|
| $Y_a$ | $X^1$ | $X^2$ | Ar | $IC_{50}$ | $R_\omega$ |
| φ, c-hex | $CH_2CH_2$ | $CH_2$ | φ | ±5 | 70 |
| φ, c-hex | CHCO | $CH_2CH=CH$ | φ | ±5 | 48 |

TABLE 1-continued

Formula (1a): both Z are N; I$^1$ is 0; n$^1$ and n$^2$ are 1

| Y$_a$ | X$^1$ | X$^2$ | Ar | IC$_{50}$ | R$_\omega$ |
|---|---|---|---|---|---|
| φ, c-hex | CHCH$_2$ | CH$_2$CH=CH | φ | ±5 | 90 |
| φ, c-hex | CH(CH$_2$)$_4$CO | CH$_2$CH=CH | φ | 3.9 | 20 |
| φ, c-hex | CH(CH$_2$)$_5$CO | CH$_2$CH=CH | φ | 12.2 | 0 |
| φ, c-hex | CHCO | CH$_2$ | φ | ±20 | 90 |
| c-hex, c-hex | CHCO | CH$_2$ | φ | 14.2 | 45 |
| c-hex, c-hex | CHCO | CH$_2$CH=CH | φ | 5.9 | 47 |
| c-hex, c-hex | CHCH$_2$ | CH$_2$CH=CH | φ | 10.2 | 13 |
| φ, c-hex | CH(CH$_2$)$_6$ | CH$_2$CH=CH | φ | 3.2 | 11 |
| φ, c-hex | CH(CH$_2$)$_5$ | CH$_2$CH=CH | φ | 5.9 | 0 |
| φ, c-hex | CH(CH$_2$)$_5$ | (CH$_2$)$_2$ | φ | 3.1 | 14 |
| φ, c-hex | CHCH$_2$ | CH$_2$CH=CH | φ | 10.6 | 15 |

TABLE 2

Formula (1b): both Z are N; I$^1$ is 0; n$^1$ and n$^2$ are 1

| Y$_b$ | X$^1$ | X$^2$ | Ar | IC$_{50}$ | R$_\omega$ |
|---|---|---|---|---|---|
| φ, c-hex | CH(CH$_2$)$_6$ | CH$_2$ | c-hex | 7.2 | 16 |

EXAMPLE 4

Distinguishing Inactivation

A. Transformation of HEK Cells:

N-type calcium channel blocking activity is assayed in human embryonic kidney cells, HEK 293, stably transfected with the rat brain N-type calcium channel subunits ($\alpha_{1B}$+$\alpha_{2\delta}$+$\beta_{1b}$ cDNA subunits). Alternatively, N-type calcium channels ($\alpha_{1B}$+$\alpha_{2\delta}$+$\beta_{1b}$ cDNA subunits), L-type channels ($\alpha_{1C}$+$\alpha_{2\delta}$+$\beta_{1b}$ cDNA subunits) and P/Q-type channels ($\alpha_{1A}$+$\alpha_{2\delta}$+$\beta_{1b}$ cDNA subunits) are transiently expressed in HEK 293 cells. Briefly, cells are cultured in Dulbecco's modified eagle medium (DMEM) supplemented with 10% fetal bovine serum, 200 U/ml penicillin and 0.2 mg/ml streptomycin at 37° C. with 5% CO$_2$. At 85% confluency cells are split with 0.25% trypsin/1 mM EDTA and plated at 10% confluency on glass coverslips. At 12 hours the medium is replaced and the cells transiently transfected using a standard calcium phosphate protocol and the appropriate calcium channel cDNAs. Fresh DMEM is supplied and the cells transferred to 28° C./5% CO$_2$. Cells are incubated for 1 to 2 days to whole cell recording.

B. Measurement of Inhibition:

Whole cell patch clamp experiments are performed using an Axopatch 200B amplifier (Axon Instruments, Burlingame, Calif.) linked to a personal computer equipped with pCLAMP software. The external and internal recording solutions contain, respectively, 5 mM BaCl$_2$, 1 mM MgCl$_2$, 10 mM HEPES, 40 mM TEACl, 10 mM glucose, 87.5 mM CsCl (pH 7.2) and 108 mM CsMS, 4 mM MgCl$_2$, 9 mM EGTA, 9 mM HEPES (pH 7.2). Currents are typically elicited from a holding potential of –80 mV to +10 mV using Clampex software (Axon Instruments). Typically, currents are first elicited with low frequency stimulation (0.03 Hz) and allowed to stabilize prior to application of the compounds. The compounds are then applied during the low frequency pulse trains for two to three minutes to assess tonic block, and subsequently the pulse frequency is increased to 0.2 Hz to assess frequency dependent block. Data are analyzed using Clampfit (Axon Instruments) and SigmaPlot 4.0 (Jandel Scientific).

What is claimed is:

1. A method to treat conditions associated with abnormal N-type calcium channel activity in a subject which method comprises administering to a subject in need of such treatment a compound of the formula

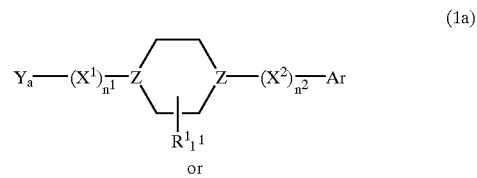

(1a)

or

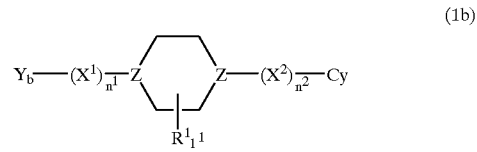

(1b)

or the salts thereof, wherein, each of Z$^1$ and Z$^2$ is independently N or CH, but one of Z$^1$ and Z$^2$ must be N;

wherein n$^1$ is 1 and n$^2$ is 0 or 1;

X$^1$ and X$^2$ are straight chain linkers;

Ar represents one or two substituted or unsubstituted aromatic or heteroaromatic single rings, and Cy represents one or two substituted or unsubstituted aliphatic cyclic or heterocyclic single rings, or consists of one substituted or unsubstituted aliphatic cyclic or heterocyclic single ring and one substituted or unsubstituted aromatic or heteroaromatic single ring;

each of Y$_a$ and Y$_b$ is two substituted or unsubstituted aromatic or heteroaromatic single rings, or can be two substituted or unsubstituted aliphatic cyclic or heterocyclic single rings or consists of one substituted or unsubstituted aliphatic cyclic or heterocyclic single ring and one substituted or unsubstituted aromatic or heteroaromatic single ring;

with the proviso that said rings of Y$_a$ cannot both be phenyl when Ar represents a single phenyl ring and X$^1$ contains less than 5C;

and with the proviso that formula (1b) must contain at least one aromatic or heteroaromatic ring;

1$^1$ is 0 or 1;

R$^1$ is substituted or unsubstituted alkyl (1–6C), substituted or unsubstituted aryl (6–10C) or substituted or unsubstituted arylalkyl (7–16C) optionally containing 1–4 heteroatoms selected from the group consisting of halo, N, P, O, and S or may independently be halo, OR, SR, NR$_2$, OOCR, NROCR, COR, COOR, CONR$_2$, CF$_3$, OCF$_3$, CN or NO$_2$, wherein R is H or alkyl (1–6C).

2. The method of claim 1 wherein Ar represents one or two unsubstituted phenyl moieties.

3. The method of claim 1 wherein n$^2$ is 1 and X$^2$ represents a linker which spaces Ar from Z$^2$ at a distance of 3–20 Å.

4. The method of claim 3 wherein X$^2$ contains at least one heteroatom selected from N and O.

5. The method of claim 3 wherein Ar represents one unsubstituted phenyl moiety and X$^2$ represents —(CH$_2$)$_{1-8}$— or —(CH$_2$)$_{1-5}$—CH=CH—(CH$_2$)$_{0-3}$— or —NH(CH$_2$)$_{1-6}$—.

6. The method of claim 3 wherein Ar represents two phenyl moieties and X$^2$ is of the formula —(CH$_2$)$_{0-6}$—CH.

7. The method of claim 1 wherein Cy represents one or two unsubstituted cyclohexyl moieties or an unsubstituted cyclohexyl moiety and an unsubstituted phenyl moiety.

8. The method of claim 7 wherein $n^2$ is 1 and $X^2$ represents a linker which spaces Cy from $Z^2$ at a distance of 3–20 Å.

9. The method of claim 8 wherein $X^2$ contains at least one heteroatom selected from N and O.

10. The method of claim 8 wherein Cy is a cyclohexyl moiety, and $X^2$ represents —$(CH_2)_{1-8}$—, —$(CH_2)_{1-5}$—CH=CH—$(CH_2)_{0-3}$— or —$NH(CH_2)_{1-6}$—.

11. The method of claim 8 wherein Cy represents two cyclohexyl moieties or a cyclohexyl moiety and a phenyl moiety.

12. The method of claim 11 wherein $X^2$ is —$(CH_2)_{0-6}$—CH—.

13. The method of claim 1 wherein $1^1$ is 0.

14. The method of claim 1 wherein $X^1$ represents a linker which spaces the $Y_a$ and $Y_b$ from $Z^1$ at a distance of 3–20 Å.

15. The method of claim 14 wherein $X^1$ contains at least one heteroatom selected from O and N.

16. The method of claim 15 wherein $X^1$ represents $CH(CH_2)_{0-6}$ or —$CH(CH_2)_{1-6}CO$.

17. A pharmaceutical composition for use in treating conditions characterized by abnormal N-type calcium channel activity which composition comprises, in admixture with a pharmaceutically acceptable excipient, a dosage amount of a compound of the formula

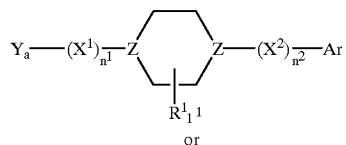

(1a)

or

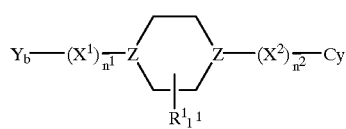

(1b)

or the salts thereof,
wherein each $Z^1$ and $Z^2$ is independently N or CH, but one of $Z^1$ and $Z^2$ must be N;
wherein $n^1$ is 1 and $n^2$ is 0 or 1;
$X^1$ and $X^2$ are straight chain linkers;
Ar represents one or two substituted or unsubstituted aromatic or heteroaromatic single rings, and
Cy represents one or two substituted or unsubstituted aliphatic cyclic or heterocyclic single rings, or consists of one substituted or unsubstituted aliphatic cyclic or heterocyclic single ring and one substituted or unsubstituted aromatic or heteroaromatic single ring;
each of $Y_a$ and $Y_b$ is two substituted or unsubstituted aromatic or heteroaromatic single rings, or can be two substituted or unsubstituted aliphatic cyclic or heterocyclic single rings or consists of one substituted or unsubstituted aliphatic cyclic or heterocyclic single ring and one substituted or unsubstituted aromatic or heteroaromatic single ring;
with the proviso that said rings of $Y_a$ cannot both be phenyl when both Ar represents a single phenyl ring and $X^1$ contains less than 5C;

and with the proviso that formula (1b) must contain at least one aromatic or heteroaromatic ring;
$1^1$ is 0 or 1;
$R^1$ is substituted or unsubstituted alkyl (1–6C), substituted or unsubstituted aryl (6–10C) or substituted or unsubstituted arylalkyl (7–16C) optionally containing 1–4 heteroatoms selected from the group consisting of halo, N, P, O, and S or may independently be halo, OR, SR, $NR_2$, OOCR, NROCR, COR, COOR, $CONR_2$, $CF_3$, CN or $NO_2$, wherein R is H or alkyl (1–6C).

18. A library comprising at least ten different compounds of the formula

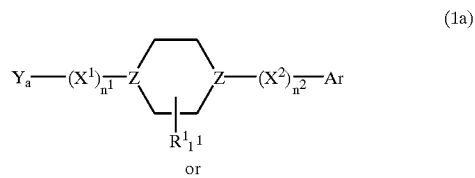

(1a)

or

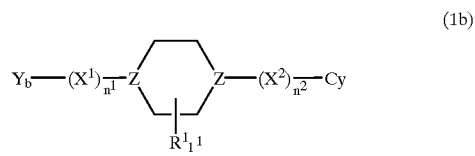

(1b)

or the salts thereof,
wherein each Z is independently N or CH, but one Z must be N;
wherein $n^1$ is 1 and $n^2$ is 0 or 1;
$X^1$ and $X^2$ are linkers;
Ar represents one or two substituted or unsubstituted aromatic or heteroaromatic rings, and
Cy represents one or two substituted or unsubstituted aliphatic cyclic or heterocyclic rings, or consists of one substituted or unsubstituted aliphatic cyclic or heterocyclic ring and one substituted or unsubstituted aromatic or heteroaromatic ring;
each of $Y_a$ and $Y_b$ is two substituted or unsubstituted aromatic or heteroaromatic rings, or can be two substituted or unsubstituted aliphatic cyclic or heterocyclic rings or consists of one substituted or unsubstituted aliphatic cyclic or heterocyclic ring and one substituted or unsubstituted aromatic or heteroaromatic ring;
with the proviso that said rings cannot both be phenyl when both Ar includes a single phenyl ring and $X^1$ contains less than 5C;
and with the proviso that formula (1b) must contain at least one aromatic or heteroaromatic ring;
$1^1$ is 0 or 1;
$R^1$ is substituted or unsubstituted alkyl (1–6C), substituted or unsubstituted aryl (6–10C) or substituted or unsubstituted arylalkyl (7–16C) optionally containing 1–4 heteroatoms selected from the group consisting of halo, N, P, O, and S or may independently be halo, OR, SR, $NR_2$, OOCR, NROCR, COR, COOR, $CONR_2$, $CF_3$, CN or $NO_2$, wherein R is H or alkyl (1–6C).

19. A method to identify a compound which antagonizes a target receptor which method comprises contacting host cells displaying said target receptor in the presence of an agonist for said receptor and with the members of the library of claim 18;
assessing the ability of the members of the library to affect the response of the receptor to its agonist; and identifying as an antagonist any member of the library which diminishes the response of the receptor to its agonist.

20. The method of claim 19 wherein the receptor is an ion channel.

21. The method of claim 20 wherein the receptor is a calcium ion channel.

22. The method of claim 21 wherein the calcium ion channel is an N-type calcium ion channel.

23. A method to treat conditions associated with abnormal calcium channel activity in a subject which method comprises administering to a subject in need of such treatment a compound of the formula

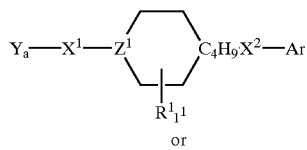

(1a)

or

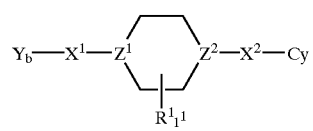

(1b)

or the salts thereof, wherein, each of $Z^1$ and $Z^2$ is independently N or CH, but one of $Z^1$ and $Z^2$ must be N;

$X^1$ is a straight chain linker that spaces $Y_a$ or $Y_b$ from $Z^1$ a distance of 3–20 Å, and $X^2$ is selected from the group consisting of $(CH_2)_{1-8}$, $(CH_2)_{1-5}CO(CH_2)_{0-3}$, $(CH_2)_{1-5}NH(CH_2)_{0-3}$, $(CH_2)_{0-5}CONH(CH_2)_{0-3}$, $—(CH_2)_{0-5}CH=CH(CH_2)_{0-3}—$ and $(CH_2)_{1-5}NHCO(CH_2)_{0-3}$, with accommodation as required for two rings;

Ar represents one or two substituted or unsubstituted aromatic or heteroaromatic single rings, and Cy represents one or two substituted or unsubstituted aliphatic cyclic or heterocyclic single rings, or consists of one substituted or unsubstituted aliphatic cyclic or heterocyclic single ring and one substituted or unsubstituted aromatic or heteroaromatic single ring;

each of $Y_a$ and $Y_b$ is two substituted or unsubstituted aromatic or heteroaromatic single rings, or can be two substituted or unsubstituted aliphatic cyclic or heterocyclic single rings or consists of one substituted or unsubstituted aliphatic cyclic or heterocyclic single ring and one substituted or unsubstituted aromatic or heteroaromatic single ring;

with the proviso that said rings of $Y_a$ cannot both be phenyl when Ar represents a single phenyl ring, $X^1$ contains less than 5C, and $X^2$ is $—(CH_2)^-{}_{1-8}$ or $—(CH_2)_{1-5}CH=CH(CH_2)^-{}_{0-3}$;

and with the proviso that formula (1b) must contain at least one aromatic or heteroaromatic ring;

$1^1$ is 0 or 1;

$R^1$ is substituted or unsubstituted alkyl (1–6C), substituted or unsubstituted aryl (6–10C) or substituted or unsubstituted arylalkyl (7–16C) optionally containing 1–4 heteroatoms selected from the group consisting of halo, N, P, O, and S or may independently be halo, OR, SR, $NR_2$, OOCR, NROCR, COR, COOR, $CONR_2$, $CF_3$, $OCF_3$, CN or $NO_2$, wherein R is H or alkyl (1–6C).

24. The method of claim 23 wherein Ar represents one or two unsubstituted phenyl moieties.

25. The method of claim 24 wherein Ar represents one unsubstituted phenyl moiety and $X^2$ represents $—(CH_2)_{1-8}—$ or $—(CH_2)_{1-5}—CH=CH—(CH_2)_{0-3}—$ or $—NH(CH_2)_{1-6}—$.

26. The method of claim 25 wherein Ar represents two phenyl moieties and $X^2$ is of the formula $—(CH_2)_{0-6}—CH$.

27. The method of claim 23 wherein Cy represents one or two unsubstituted cyclohexyl moieties or an unsubstituted cyclohexyl moiety and an unsubstituted phenyl moiety.

28. The method of claim 27 wherein Cy is a cyclohexyl moiety, and $X^2$ represents $—(CH_2)_{1-8}—$, $—(CH_2)_{1-5}—CH=CH—(CH_2)_{0-3}—$ or $—NH(CH_2)_{1-6}—$.

29. The method of claim 27 wherein Cy represents two cyclohexyl moieties or a cyclohexyl moiety and a phenyl moiety.

30. The method of claim 23 wherein $X^2$ is $—(CH_2)_{0-6}—CH—$.

31. The method of claim 23 wherein $1^1$ is 0.

32. A pharmaceutical composition for use in treating conditions characterized by abnormal calcium channel activity which composition comprises, in admixture with a pharmaceutically acceptable excipient, a dosage amount of a compound of the formula

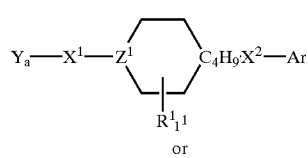

(1a)

or

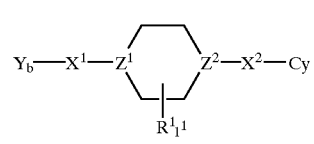

(1b)

or the salts thereof, wherein, each of $Z^1$ and $Z^2$ is independently N or CH, but one of $Z^1$ and $Z^2$ must be N;

$X^1$ is a straight chain linker that spaces $Y_a$ or $Y_b$ from $Z^1$ a distance of 3–20Å, and $X^2$ is selected from the group consisting of $(CH_2)_{1-8}$, $(CH_2)_{1-5}CO(CH_2)_{0-3}$, $(CH_2)_{1-5}NH(CH_2)_{0-3}$, $(CH_2)_{0-5}CONH(CH_2)_{0-3}$, $—(CH_2)_{0-5}CH=CH(CH_2)_{0-3}—$ and $(CH_2)_{1-5}NHCO(CH_2)_{0-3}$, with accommodation as required for two rings;

Ar represents one or two substituted or unsubstituted aromatic or heteroaromatic single rings, and Cy represents one or two substituted or unsubstituted aliphatic cyclic or heterocyclic single rings, or consists of one substituted or unsubstituted aliphatic cyclic or heterocyclic single ring and one substituted or unsubstituted aromatic or heteroaromatic single ring;

each of $Y_a$ and $Y_b$ is two substituted or unsubstituted aromatic or heteroaromatic single rings, or can be two substituted or unsubstituted aliphatic cyclic or heterocyclic single rings or consists of one substituted or unsubstituted aliphatic cyclic or heterocyclic single ring and one substituted or unsubstituted aromatic or heteroaromatic single ring;

with the proviso that said rings of $Y_a$ cannot both be phenyl when Ar represents a single phenyl ring, $X^1$ contains less than 5C, and $X^2$ is $—(CH_2)^-{}_{1-8}$ or $—(CH_2)_{0-5}CH=CH(CH_2)^-{}_{0-3}$;

and with the proviso that formula (1b) must contain at least one aromatic or heteroaromatic ring;

$1^1$ is 0 or 1;

$R^1$ is substituted or unsubstituted alkyl (1–6C), substituted or unsubstituted aryl (6–10C) or substituted or unsubstituted arylalkyl (7–16C) optionally containing 1–4 heteroatoms selected from the group consisting of halo, N, P, O, and S or may independently be halo, OR, SR, NR$_2$, OOCR, NROCR, COR, COOR, CONR$_2$, CF$_3$, OCF$_3$, CN or NO$_2$, wherein R is H or alkyl (1–6C).

33. A method to treat conditions associated with abnormal calcium channel activity in a subject which method comprises administering to a subject in need of such treatment a compound of the formula

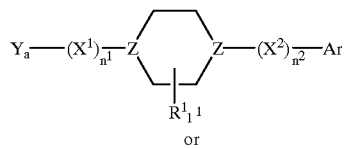

(1a)

or

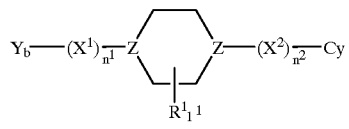

(1b)

or the salts thereof,
wherein, each of $Z^1$ and $Z^2$ is independently N or CH, but one of $Z^1$ and $Z^2$ must be N;
wherein $n^1$ is 1 and $n^2$ is 0 or 1;
$X^1$ and $X^2$ are straight chain linkers;
Ar represents one or two substituted or unsubstituted heteroaromatic single rings or two substituted or unsubstituted aromatic or heteroaromatic single rings, and
Cy represents two substituted or unsubstituted aliphatic cyclic single rings or one or two substituted or unsubstituted heterocyclic single rings, or consists of one substituted or unsubstituted aliphatic cyclic or heterocyclic single ring and one substituted or unsubstituted aromatic or heteroaromatic single ring;
each of $Y_a$ and $Y_b$ is two substituted or unsubstituted aromatic or heteroaromatic single rings, or can be two substituted or unsubstituted aliphatic cyclic or heterocyclic single rings or consists of one substituted or unsubstituted aliphatic cyclic or heterocyclic single ring and one substituted or unsubstituted aromatic or heteroaromatic single ring;
with the proviso that said rings of $Y_a$ cannot both be phenyl when both Ar represents a single phenyl ring and $X^1$ contains less than 5C;
and with the proviso that formula (1b) must contain at least one aromatic or heteroaromatic ring;

$1^1$ is 0 or 1;

$R^1$ is substituted or unsubstituted alkyl (1–6C), substituted or unsubstituted aryl (6–10C) or substituted or unsubstituted arylalkyl (7–16C) optionally containing 1–4 heteroatoms selected from the group consisting of halo, N, P, O, and S or may independently be halo, OR, SR, NR$_2$, OOCR, NROCR, COR, COOR, CONR$_2$, CF$_3$, OCF$_3$, CN or NO$_2$, wherein R is H or alkyl (1–6C).

34. The method of claim 33 wherein Ar represents two phenyl moieties.

35. The method of claim 32 wherein $n^2$ is 1 and $X^2$ represents a linker which spaces Ar from $Z^2$ at a distance of 3–20Å.

36. The method of claim 35 wherein $X^2$ contains at least one heteroatom selected from N and 0.

37. The method of claim 33 wherein $X^2$ is of the formula —(CH$_2$)$_{0-6}$—CH.

38. The method of claim 33 wherein Cy represents two unsubstituted cyclohexyl moieties or an unsubstituted cyclohexyl moiety and an unsubstituted phenyl moiety.

39. The method of claim 38 wherein $n^2$ is 1 and $X^2$ represents a linker which spaces Cy from $Z^2$ at a distance of 3–20Å.

40. The method of claim 39 wherein $X^2$ contains at least one heteroatam selected from N and 0.

41. The method of claim 38 wherein $X^2$ is —(CH$_2$)$_{0-6}$—CH—.

42. The method of claim 33 wherein $1^1$ is 0.

43. The method of claim 33 wherein $X^1$ represents a linker which spaces the $Y_a$ or $Y_b$ from $Z^1$ at a distance of 3–20Å.

44. The method of claim 43 wherein $X^1$ contains at least one heteroatom selected from O and N.

45. The method of claim 44 wherein $X^1$ represents CH(CH$_2$)$_{0-6}$ or —CH(CH$_2$)$_{1-6}$CO.

46. A pharmaceutical composition for use in treating conditions characterized by abnormal calcium channel activity which composition comprises, in admixture with a pharmaceutically acceptable excipient, a dosage amount of a compound of the formula

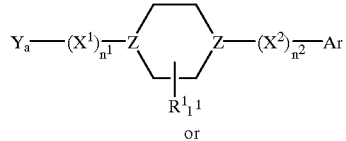

(1a)

or

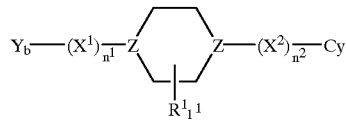

(1b)

or the salts thereof,
wherein, each of $Z^1$ and $Z^2$ is independently N or CH, but one of $Z^1$ and $Z^2$ must be N;
wherein $n^1$ is 1 and $n^2$ is 0 or 1;
$X^1$ and $X^2$ are straight chain linkers;
Ar represents one or two substituted or unsubstituted heteroaromatic single rings or two substituted or unsubstituted aromatic or heteroaromatic single rings, and
Cy represents two substituted or unsubstituted aliphatic cyclic single rings or one or two substituted or unsubstituted heterocyclic single rings, or consists of one substituted or unsubstituted aliphatic cyclic or heterocyclic single ring and one substituted or unsubstituted aromatic or heteroaromatic single ring;
each of $Y_a$ and $Y_b$ is two substituted or unsubstituted aromatic or heteroaromatic single rings, or can be two substituted or unsubstituted aliphatic cyclic or heterocyclic single rings or consists of one substituted or unsubstituted aliphatic cyclic or heterocyclic single ring and one substituted or unsubstituted aromatic or heteroaromatic single ring;

with the proviso that said rings of $Y_a$ cannot both be phenyl when Ar represents a single phenyl ring, $X^1$ contains less than 5C;

and with the proviso that formula (1b) must contain at least one aromatic or heteroaromatic ring;

$1^1$ is 0 or 1;

$R^1$ is substituted or unsubstituted alkyl (1–6C), substituted or unsubstituted aryl (6–10C) or substituted or unsubstituted arylalkyl (7–16C) optionally containing 1–4 heteroatoms selected from the group consisting of halo, N, P, O, and S or may independently be halo, OR, SR, $NR_2$, OOCR, NROCR, COR, COOR, $CONR_2$, $CF_3$, $OCF_3$, CN or $NO_2$, wherein R is H or alkyl (1–6C).

* * * * *

UNITED STATES PATENT AND TRADEMARK OFFICE
CERTIFICATE OF CORRECTION

PATENT NO. : 6,492,375 B2
DATED : December 10, 2002
INVENTOR(S) : Terrance P. Snutch et al.

It is certified that error appears in the above-identified patent and that said Letters Patent is hereby corrected as shown below:

<u>Title page,</u>
Item [75], Inventor, the name of the second inventor should be added as follows:
-- Gerald W. Zamponi, Calgary (AT/CA) --

Signed and Sealed this

Twenty-fourth Day of August, 2004

JON W. DUDAS
*Director of the United States Patent and Trademark Office*